United States Patent [19]

Raghuprasad

[11] Patent Number: 5,186,164
[45] Date of Patent: Feb. 16, 1993

[54] MIST INHALER

[76] Inventor: Puthalath Raghuprasad, 2400 East 8th Street, Odessa, Tex. 79761

[21] Appl. No.: 656,911

[22] Filed: Mar. 15, 1991

[51] Int. Cl.$^5$ ............................................. A61M 11/00
[52] U.S. Cl. ............................ 128/200.14; 128/203.15
[58] Field of Search ................. 128/200.14, 200.23, 128/200.19, 200.22, 203.12, 203.15, 203.21, 203.16, 203.17

[56] References Cited

U.S. PATENT DOCUMENTS

| | | | |
|---|---|---|---|
| 286,666 | 10/1883 | Willis | 128/203.16 |
| 639,878 | 12/1899 | Wezel | 128/203.16 |
| 1,416,244 | 5/1922 | Thompson | 128/203.16 |
| 3,809,294 | 5/1974 | Torgeson | 128/203.15 |
| 4,674,491 | 6/1987 | Brugger et al. | 128/203.15 |

Primary Examiner—Edgar S. Burr
Assistant Examiner—Aaron J. Lewis
Attorney, Agent, or Firm—Marcus L. Bates

[57] ABSTRACT

An inhaler apparatus by which a vapor is condensed by a powder containing medication into a cloud of very fine particles that can be inhaled deep into a patient's lungs. The apparatus includes an enclosure, preferably a transparent container, which enables the patient to observe the formation of the cloud. The cloud is formed because of the provision within the enclosure of the proper pressure, moisture content, temperature, and a dust-like powder that is actually the medication and which seeds the cloud. A heater is placed adjacent a liquid to cause the liquid to heat and vaporize. A small pump reduces the pressure within the container only the amount required to achieve the proper conditions for the cloud formation. A liquid is placed in a liquid containing part of the container. The patient actuates the starting mechanism and the pump partially evacuates the transparent container; then the heating element commences vaporizing the water, after which suitable medication powder flows into the transparent container, and seeds the cloud. The cloud should form at the instant the powdered medication is introduced into the transparent container. This is the signal for the patient to inhale the cloud.

19 Claims, 2 Drawing Sheets

MIST INHALER

BACKGROUND OF THE INVENTION

The administration of medicaments directly to the lungs is accomplished mainly by two means: (a) pressurized aerosol devices, popularly known as the "inhalers" and, (b) nebulizers, or devices for generation of fine mist of medications. The former has the general advantage of being small and therefore easy to carry in a pocket and readily available for use in emergencies. However, most of them suffer from the main drawback of needing very exacting technique in using them. This makes such "inhalers" almost impossible for the very young or the very old patients and some others with problems with hand-mouth coordination. The nebulizers, on the other hand, are easy to use but suffer from the drawbacks of being large and cumbersome and expensive. In addition, they use solutions of medications in water and thus, some important medications, such as the steroids which are not water soluble, cannot be used in such nebulizers.

The present invention proposes to solve the noted problems of these two main types of inhaling devices. In doing so, an attempt is made to produce a "cloud" in a small, portable, hand held chamber. Since the "cloud" remains in the chamber and is available whenever the user wants to inhale and does not discharge from the device under significant pressure, the main drawback of the hand held inhalers is avoided. Also, because a "cloud" can be seeded using a powder selected from either water soluble or water insoluble medications, or a mixture thereof, virtually all medicines can be administered by this proposed device. Some of the other advantages of the present invention will become apparent as further details are described.

Cloud formation occurs in nature when certain atmospheric conditions are satisfied. The critical conditions are low atmospheric pressure, high humidity, somewhat low temperature, and a critical "seeding" provided in the atmosphere by the ever present particles of dust. All the above conditions come together in the higher reaches of the atmosphere, usually when sufficient humidity prevails, as the other conditions are always present at such heights. However, even at sea level clouds can form as evidenced by fog which occurs when the sum total of factors are favorable, i.e.: when enough humidity meets sufficiently cold temperature in the presence of dust. It is clear then, that with some effort, similar conditions can be reproduced in a gadget to capture this "cloud" for the general purpose of dispensing medications to the airways, and such a desirable achievement would be novel, unobvious, and useful for it would represent a great step forward in the art.

In the present invention, the above variables are brought together in a portable, hand held device in a manner conducive to the formation of a dense cloud "on demand". The steps in carrying out this process include, in sequence, rarefaction of a small air tight transparent chamber by the use of an extracting pump of sufficient power, provision of water vapor by a heating element vaporizing a small quantity of either water or saline solution, and, finally, by the introduction of small quantities of "dust" into this assembly of strategic conditions. The "dust" includes a few micro-grams of finely powdered medicine therein.

SUMMARY OF THE INVENTION

This disclosure comprehends an inhaler apparatus and method by which liquid is formed into a vapor and admixed with a suitable powdered medication that acts to seed the vapor so that a cloud-like mixture is obtained by which the medication can be translocated deep into a patient's lungs. One form of the apparatus includes an enclosure, preferably a transparent container, which enables the patient to observe the formation of a cloud of medication and condensed droplets of vapor within the container. The cloud which is formed and contained within the enclosure provides a very fine mist that can be inhaled directly into the lungs.

The cloud is formed as a result of modifying the atmosphere within the enclosure by the proper control of pressure, moisture content, temperature, and the addition of a dust-like powder that is actually the medication as well as the cloud seeding agent. Very small amounts of medication are required. The liquid preferably is water, but it may also be a saline solution because a salt solution should provide a more satisfactory cloud. There is a vaporizing means contained adjacent to the liquid to cause the liquid phase to change into the vapor phase. A small pump means reduces the pressure within the enclosure only the amount required to achieve the desired cloud.

A small amount of water or saline solution is placed within a special part of the enclosure, the chamber pressure is reduced to a value that enhances vaporization of the liquid while a suitable heating element is energized to subsequently heat the water or saline solution, and thereby brings about the conditions necessary for the formation of the cloud. A valve means is used between the chamber and a mouthpiece to isolate the contents of the container and to prevent loss of the mixture of water vapor and medication that forms the cloud.

In the preferred embodiment of the invention, the patient energizes the apparatus, whereupon the vacuum pump exhausts the cloud forming chamber, and then the heating element commences vaporizing the water and increases the humidity within the cloud forming chamber. Next, medication powder is caused to be dispersed into the transparent chamber while the chamber pressure is being equalized. Under the proposed conditions the cloud should form at the instant the powdered medication is introduced into the transparent chamber. This is the signal for the patient to position the mouthpiece into operative position so that it can be placed in his mouth and the medicated cloud inhaled through the mouthpiece.

The advantages of the apparatus are the low cost, the increased efficiency that results from the fine water mist acting as the carrying agent for the medication, the very small droplets that are produced by the condensation of the moisture, and the enhanced cloud formation as a result of seeding the contents of the container with the powdered medication. Hence, the powdered medication enhances formation of the cloud and the resultant cloud acts as an ideal vehicle for transporting the mixture deep into a person's lungs.

A primary object of the present invention is the provision of an inhaler apparatus by which a vapor containing medication is formed to provide a cloud of very fine particle size that can be inhaled deep into a patient's lungs.

Another object of the invention is to provide an inhaler apparatus by which a vaporized liquid containing medication is formed to provide a cloud of very fine mist that can be inhaled deep into a patient's lungs.

A further object of this invention is to disclose and provide an inhaler apparatus that includes an enclosure, preferably in the form of a transparent container, which enables the patient to observe the formation of a cloud of medication as it is formed and is subsequently inhaled deep into the lungs.

A still further object of this invention is to provide both method and apparatus by which a medicated cloud is formed within an enclosure by seeding a controlled atmosphere of water vapor and air with a powdered medicine, and then the cloud is inhaled.

Another and still further object of this invention is the provision of method and apparatus by which a cloud-like mixture of powdered medicine and water vapor is formed within an enclosure having therein the proper pressure, moisture content, temperature, and means by which a dust-like powder, that is actually the medication, is introduced into the enclosure to enhance the formation of the cloud. The cloud is then inhaled into the lungs.

An additional object of the present invention is the provision of apparatus by which a cloud-like mixture is formed within an enclosure by adjusting a moisture laden atmosphere contained therein to the proper pressure, moisture content, and temperature, and by which a dust-like powder, containing a suitable medication, is introduced into the enclosure to seed the particles and form the cloud.

Another and still further object of the present invention is to provide a mist inhaler apparatus that uses ecologically compatible inhalants and avoids the undesirable use of halogenated propellants by the provision of apparatus by which water miscible medication, water non-miscible medication, or a combination thereof can be incorporated into a cloud of vapor and inhaled into the lungs.

These and other objects and advantages of the invention will become readily apparent to those skilled in the art upon reading the following detailed description and claims and by referring to the accompanying drawings.

The above objects are attained in accordance with the present invention by the provision of a method for use with apparatus fabricated a manner substantially as described herein.

DETAILED DESCRIPTION OF THE PREFERRED EMBODIMENT

Figure 1:
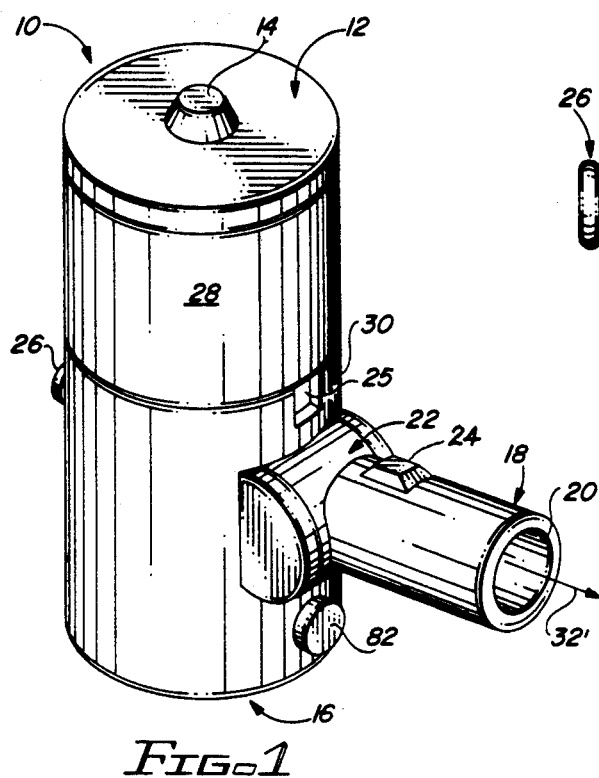
FIG. 1 is a perspective side view of one of many possible embodiments of this invention.

The figures of the drawings disclose several different embodiments of a mist inhaler made in accordance with this invention. Broadly, as seen in FIG. 1, for example, the invention comprises mist inhaler apparatus 10 for creating a very fine cloud-like medicated mist within a transparent enclosure. The enclosure includes a top 12, a switch 14, and a bottom 16. The mist inhaler apparatus 10 includes a pivotally mounted outlet valve assembly and mouthpiece 18. The valve assembly and mouthpiece 18 has an outlet 20 of a size to be conveniently received within one's mouth. A socket assembly 22 forms a main outlet valve device for controlling flow through the mouthpiece 18. A valve element 24 is formed on the exterior of mouthpiece 18 that cooperates with an equalizer valve seat 25.

A charge valve assembly 26 is mounted on the apparatus for controlling flow of medicated powder thereinto and forms a means for introducing a charge of powder into mist inhaler apparatus 10 to thereby seed the vapor to form a medicated cloud. The mist inhaler apparatus 10 includes an upper enclosure 28 located above a lower enclosure 30. Note in FIG. 2 that a cloud 32 is being formed within a chamber 62 of the transparent lower enclosure 30 and, in FIG. 6, for purpose of illustration, the cloud 32 is shown exiting the mouthpiece 18 as it is translocated into the lungs (not shown). Hence, a medicated cloud is formed within cloud forming chamber 62 where it is available for inhaling and thereby treating the lungs.

Figure 5:
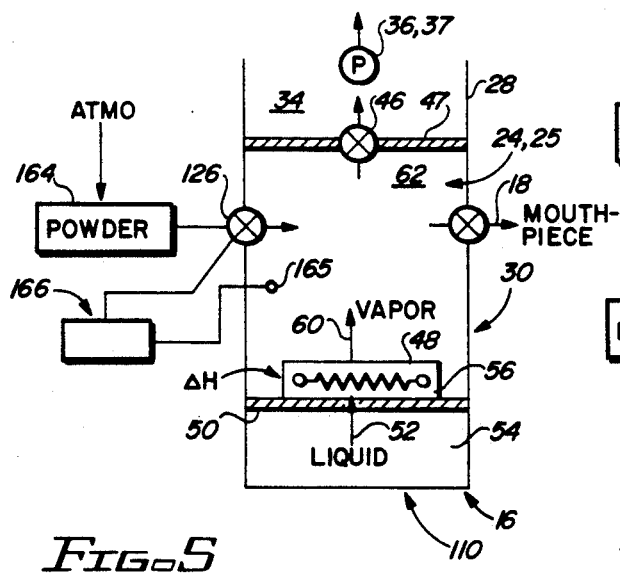
FIG. 5 is a part diagrammatical, part schematical, part cross-sectional view of another possible embodiment of this invention; and, FIG. 6 is a part diagrammatical, part schematical, part cross-sectional view of still another of many possible embodiments of this invention.
Figure 6:
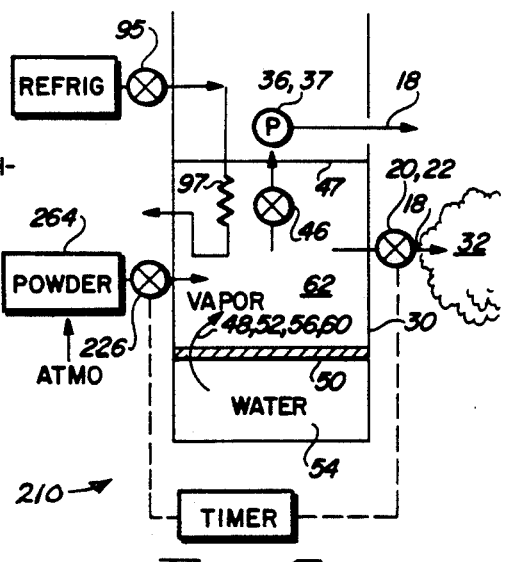
Figure 2:
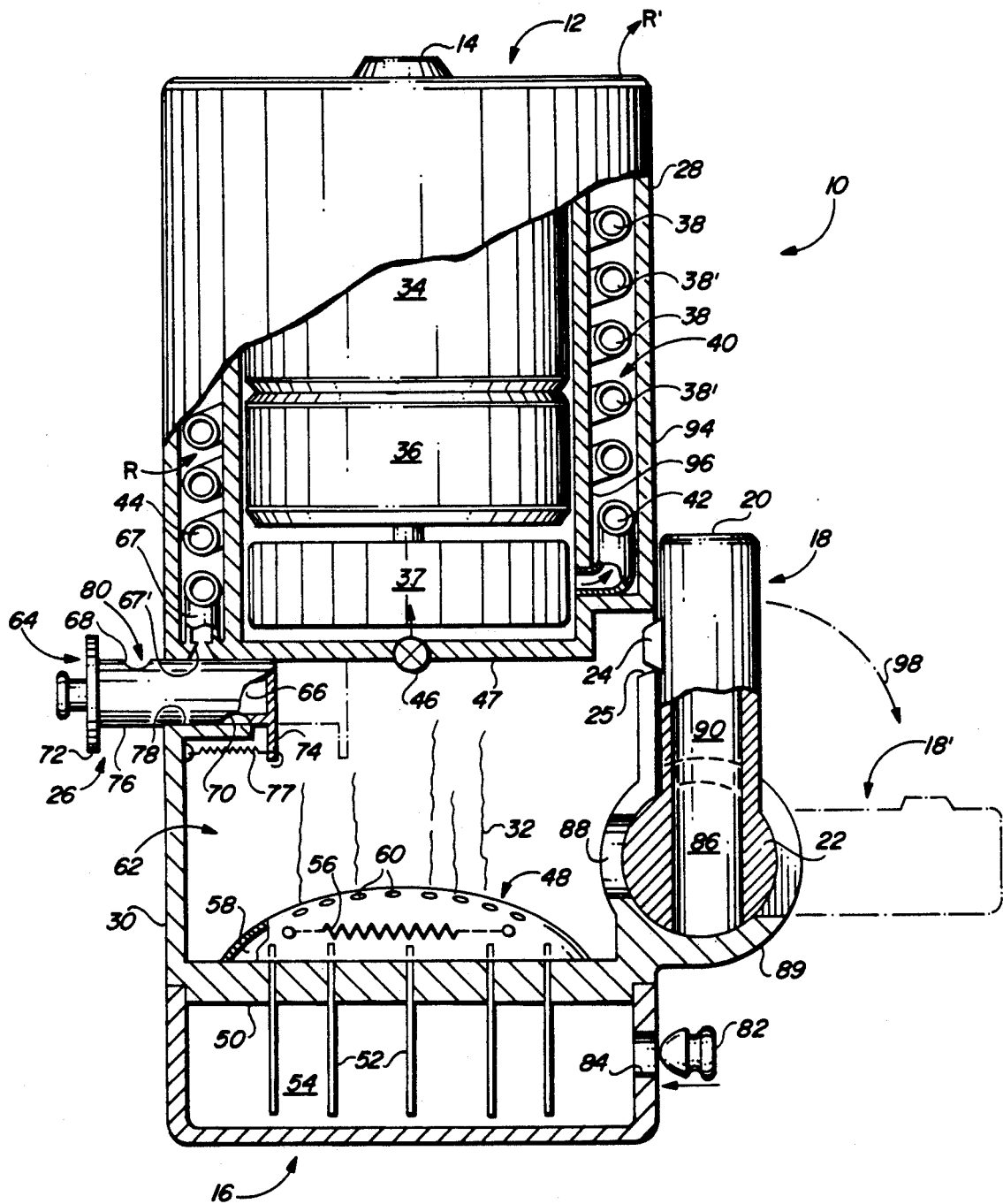
FIG. 2 is a longitudinal, part cross-sectional view of the apparatus disclosed in FIG. 1.

As best illustrated in FIGS. 2, 5 and 6, upper enclosure 28 houses a power supply in the form of a battery 34. A pump means having a motor 36 connected to a blower 37 is arranged for lowering the pressure within lower chamber 62 which underlies the battery. A cooling and storage coil 38, 38' is wound about the interior of the walls that form a cooling annulus 40 within upper enclosure 28. The pump means 36, 37 exhausts into the inlet 42 of coil 38. The coil 38 spirals up while coil 38' spirals down to terminate at an outlet 44.

A check valve 46 is supported in a partition wall 47. The wall 47 separates upper enclosure 28 from lower enclosure 30. A dome 48 is supported from partition wall 50. A plurality of small capillary tubes 52 are supported by wall 50 and extend from the lower end of a liquid container 54 into the interior of the dome 48. A heater 56 is mounted within the interior 58 of the dome 48 in close proximity to the outlet ends of the capillary tubes where at least part of the liquid can flow from liquid container 54 and spray onto heater 56, where the liquid is vaporized. The fluid sprays through the capillary tube by the suction action exerted by the negative pressure within lower chamber 62. Dome 48 has perforations 60 through which vaporized liquid contained within the dome interior can flow into lower chamber 62.

The charge valve assembly 26 includes a reciprocating, sliding valve element in the form of a hollow cylinder 64 which has a charge containing interior 66, charge inlet 68, outlet port 70, and opposed stop means 72, 74. The hollow cylinder 64 has a cylindrical body at 76 and is slidably received in a reciprocating and sealed manner within a cylindrical passageway 78. The charge valve 26 is illustrated in the closed position in FIG. 2, and is ready to receive a charge 80 through charge inlet 68 so that the powder charge can be stored in the hollow cylinder 64.

Figure 3:
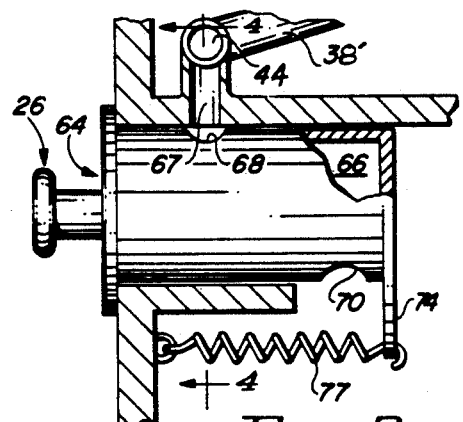
FIG. 3 is a fragmented, enlarged, cross-sectional, detailed view showing part of the apparatus of FIG. 2 in an alternate configuration of operation.
Figure 4:
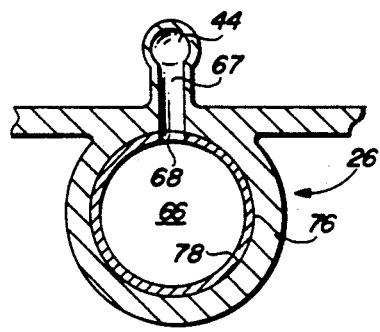
FIG. 4 is a fragmented, cross-sectional view of FIG. 3.

As seen in FIG. 3, when the hollow cylinder 64 is actuated to the alternate position, the charge port or inlet 68 is aligned with coil discharge 67, while powder outlet port 70 is uncovered as it is moved to the right and into communication with lower chamber 62 as shown in FIG. 3 and as suggested in dot dash lines in FIG. 2. The hollow cylinder 64 will move from the position of FIG. 2 into the position of FIG. 3 when the pressure differential thereacross reaches a suitable magnitude to overcome the force of spring 77 which holds the charge valve element 24 in its neutral or standby position. It can also be moved by depressing it with the finger.

The coil outlet 67 is provided with an orifice 67' to achieve a suitable pressure drop thereacross which enhances dispersement of the powder from charge valve assembly 26 into lower chamber 62, and also effects a expansion of the air as it enters sudden chamber 62 thus cooling the air. A plug 82 forms a closure member for port 84 and can be removed to fill liquid container 54.

The pivotal outlet valve assembly and mouthpiece 18 of FIG. 2 is illustrated in the retracted or closed position, and assumes the open position when rotated into the dot-dash open position 18'. There is a passageway 86 formed in socket assembly 22 that is aligned with port 88 of housing 89. Hence, the valve assembly and mouthpiece 18, when rotated, as indicated by the arrow at numeral 98, into the open position 18', aligns outlet flow port 86 and passageways 88 and 90 to form a flow path from lower chamber 62 to mouthpiece outlet 20.

Rotation of the valve assembly and mouthpiece 18 into position 18' also removes valve element 24 from valve seat 25 and allows ambient air to flow into lower chamber 62 and thereby displaces the formed cloud 32 as chamber air is sucked through valve assembly and mouthpiece 18. R, R' indicate flow of refrigerant through annulus 40 for cooling the contents of coils 38 and 38', if desired.

It will be noted that coil 38, 38' acts as a storage vessel, the contents of which will cool during residence therein due to the increased pressure thereof as the contents of lower chamber 62 is pumped at 36, 37, 46, 42 thereinto. Hence there is a heat loss associated with the transferred liquid which later effects a lowering of the temperature of the chamber contents, because subsequent return flow from coil 38, 38' through charge valve assembly 26, back into lower chamber 62 is occasioned by a pressure drop across orifice 67'. This provides a cooling of the returned atmosphere due to the Joule-Thompson effect.

Where additional cooling is required, a refrigerant can be introduced at R, R' into annulus 40 to further reduce the temperature of the coil and the contents thereof. The cooling annulus 40 is formed between outer circular wall members 94 and 96.

In the embodiment illustrated in FIG. 5, a wall 47 is located between the upper and lower enclosures 28 and 30 and supports the one way check valve 46 therein. The check valve 46 allows the pump means 36, 37 to establish a reduced pressure within the cloud forming chamber 62 and maintain it without extracting the humidity that subsequently results in the formation of the cloud 32 therewithin. The charge valve assembly 126 is actuated by the controller 166 which causes charge valve assembly 126 to transfer a predetermined quantity of medicated powder from the illustrated hollow cylinder 164 into lower chamber 62 to thereby seed the atmosphere contained within the lower chamber upon the pressure within the chamber 62 being reduced to a predetermined magnitude. The cooling coil 38, 38' is not included in the embodiment of FIG. 5, the coil being an optional detail of the invention that preferably is eliminated where possible to do so.

The liquid at 54 may be a saline solution of water because a salt solution provides a more satisfactory cloud. The electrical heating apparatus 56 can take on a number of different forms, but preferably is a resistance heating element contained adjacent the liquid to cause the liquid to impinge thereon and thereby heat and vaporize when switch 14 (not shown) is depressed. The pump means 36, 37 can be a manually or electrically actuated device that reduces the pressure only the amount required to achieve a satisfactory cloud. It is usually unnecessary to cool the chamber below ambient and such additional apparatus is absent from the embodiment of FIG. 5 because this represents another technical factor of refrigeration and further complicates the apparatus.

A saline solution is placed in liquid container 54, a suitable medicated powder is placed in the hollow cylinder 164, the pump means 36, 37 is energized to produce a vacuum in lower chamber 62, and then the heating element 56 is energized to vaporize liquid. The illustrated one way check valve 46 is used between the vacuum pump means and lower chamber 62 to prevent loss of the rarified atmosphere after the conditions for cloud formation have been satisfied. At that time sensor 165 tells the controller 166 to actuate the charge valve assembly 126, whereupon opening of the valve allows a flow of a mixture of atmospheric air and powdered medication into lower chamber 62, and the medicated cloud-like vapor is formed. The sensor 165 and charge valve assembly 126 can be a spring loaded valve apparatus arranged to assume the open position when the pressure differential thereacross reaches a predetermined magnitude.

The mist inhaler illustrated in FIG. 6 comprehends apparatus 210 by which a cloud-like vapor 32 containing medication is formed and can subsequently be transported deep into one's lungs by inhaling. The transparent enclosure 30 that forms lower chamber 62 enables the patient to observe the formation of a cloud of medication therewithin. The cloud 32 is formed as a result of the presence of a controlled atmosphere contained within the lower chamber 62 which is adjusted to the proper pressure, moisture content and temperature, along with a dust-like powder at 264 that is actually the medication which advantageously is used for seeding the contained atmosphere. Very small amounts of medication are required (milligrams or less).

Cooling valve 95 of FIG. 6 controls flow of refrigeration to cooling coil 97 when required. The timer of FIG. 6 first energizes pump means 36, 37 and then energizes vaporizer 48, 52, 56, 60; thereafter, powder charge valve assembly 226 is opened to seed the cloud. Then valve assembly and mouthpiece 18 is opened.

Those skilled in the art will appreciate that cloud formation within the cloud forming chamber 62 is achieved by adjusting all of the variables thereof in a manner to enhance formation of the medicated cloud. This includes the method or process of providing a proper quantity of water or other selected liquid within a confined space, at a temperature and pressure to assure vaporization of the liquid. The formation of water vapor is enhanced by lowering the chamber pressure so that when powdered medication is subsequently introduced into the space, the medicated powder acts as a seeding agent which enhances formation of the liquid particles that form the cloud due to its particle size and surface.

In operation of FIG. 2, the patient places a medicated powder charge 80 in the hollow cylinder 64 and then pushes down on switch 14 for starting the mechanism. This causes motor 36 to be activated which operates air pump 37 to partially evacuate lower chamber 62 of the transparent enclosure 30. The heating element 56 is energized and commences vaporizing the water which has been forced through the capillary tubes 52 due to the pressure differential thereacross. Next the hollow cylinder 64 containing medication powder is connected by movement of the charge valve assembly 26 into the position of FIG. 3, so that the contents thereof flow into the transparent lower chamber 62 due to flow of the high pressure fluid from coils 38, 38'. The cloud should form at the instant the powdered medication is introduced into the transparent chamber and as equilibrium is achieved. This is the signal for the patient to rotate valve assembly and mouthpiece 18 into position 18' and inhale the cloud.

Some of the advantages of the disclosed apparatus are the provision of a workable, non-pressurized, portable unit that produces a medicinal mist or cloud of water vapor that is of a very fine particle size which makes available to the patient an improved medicinal charge of material that enhances the likelihood of the charge being inhaled deeply into the lungs; as contrasted to known aerosol inhalers that discharge the dose at high pressure which makes it difficult to get most of the metered dose into the lungs, even when perfect inhaling technique is employed by the patient. Further, any mixture of known treatment medicine, including water and oil soluble lung treatment substances, can also be used at the same time with the present invention. Moreover, since the units made in accordance with this invention are perpetually reusable, and the only significant cost is the replacement of the medicinal powder, a lower cost of delivering inhaled medicines deep into the lungs in a more efficient and economical manner is achieved with the present method and apparatus.

I claim:

1. An inhaler apparatus by which a mixture of vapor and medication is formed to provide a cloud of very fine particle size that can be inhaled deep into a patient's lungs; said apparatus includes an enclosure which forms a cloud forming chamber within which a cloud of the vapor and medication can be formed;
   a liquid containing chamber in communication with said cloud forming chamber; means included in said apparatus for vaporizing at least part of any liquid that may be contained in said liquid containing chamber and thereby increase the vapor present in the cloud forming chamber, and pump means by which the cloud forming chamber pressure is reduced to a value that enhances the vaporization of the liquid and the formation of a cloud;
   cloud seeding means connected to introduce a quantity of medicated powder into said cloud forming chamber by which the powder is dispersed and said cloud is formed within the cloud forming chamber by the provision of the proper pressure, moisture content, temperature, and medicated powder; and,
   a mouthpiece connected to said inhaler apparatus through which the contents of the cloud forming chamber can flow.

2. The apparatus of claim 1 wherein a one way check valve is mounted between the pump means and the cloud forming chamber to prevent loss of the reduced pressure in the cloud forming chamber.

3. The apparatus of claim 2 wherein said enclosure is a transparent container which enables one to observe the formation of a cloud of vapor and medication.

4. The apparatus of claim 3 wherein said cloud seeding means disperses powder into the cloud forming chamber after the vapor pressure has been adjusted to increase the size of droplets formed from the vapor present in the cloud forming chamber and thereby seed the vapor and enhance cloud formation.

5. The apparatus of claim 4 wherein said mouthpiece is included for inhaling the contents of the cloud forming chamber; and further including means connected to the mouthpiece for forming an inlet from ambient into the cloud forming chamber.

6. The apparatus of claim 1 wherein said cloud seeding means are provided for dispersing powder into the cloud forming chamber after the vapor pressure has been adjusted to increase the vapor content of said cloud forming chamber and thereby seed the vapor and enhance cloud formation.

7. The apparatus of claim 6 wherein said mouthpiece is included for inhaling a cloud that may be formed within the cloud forming chamber, and a check valve means for preventing reverse flow from said pump means back into said cloud forming chamber.

8. An inhaler apparatus by which a vapor containing medication is formed to provide a cloud of very fine mist that can be inhaled deep into a patient's lungs, said apparatus includes an enclosure that forms a cloud chamber within which a cloud of medication and vapor can be formed;
   a liquid containing chamber connected to said cloud chamber, a suitable heating element, including means by which said heating element is energized to heat at least some of any liquid contained within said liquid containing chamber, and a pump means for reducing the pressure within said cloud chamber to a value that enhances the vaporization of the liquid to thereby form a cloud within said cloud chamber;
   means introducing a powdered medicament into said cloud chamber; and means including a mouthpiece by which the contents of the cloud chamber flows therethrough:
   whereby, a cloud is formed by the provision within the cloud chamber of the proper pressure, moisture content, temperature, and a powdered medicament that provides the medication and which is dispersed within the cloud chamber to seed the vaporized liquid and form a cloud.

9. The apparatus of claim 8 wherein a one way check valve is mounted between the pump means and the cloud chamber to prevent loss of the reduced pressure.

10. The apparatus of claim 9, wherein said enclosure is a transparent container which enables a person to observe the formation of a cloud of moisture and medication therewithin.

11. The apparatus of claim 8 wherein said means by which medicated powder is dispersed into the cloud chamber occurs after the vapor pressure has been adjusted to thereby seed the vapor and enhance cloud formation.

12. The apparatus of claim 11 wherein said mouthpiece is included for inhaling the contents of the cloud chamber; and, valve means connected to be opened in response to movement of said mouthpiece, and thereby connect said cloud chamber to ambient and to a patient's mouth.

13. The apparatus of claim 8 wherein said means introducing a powdered medicant are provided by which the powder is dispersed into the cloud chamber after the vapor pressure has been adjusted to thereby seed the vapor and enhance cloud formation; a mouthpiece is included for inhaling the contents of the cloud chamber; and valve means connected to establish flow from ambient into said cloud chamber and through said mouthpiece, said valve means is opened by movement of said mouthpiece.

14. A method of forming a cloud of vapor and medicine that can be inhaled to treat the lungs, comprising the steps of:
   isolating a liquid and evaporating a quantity of the liquid within an enclosure while adjusting the pressure within the enclosure to a value that enhances the subsequent formation of a cloud;
   arranging a quantity of treatment medicine that is in the form of a finely divided powder; said quantity of powder is selected to provide a dose of medicine for ones lungs;
   dispersing said dose of medicated powder into the evaporated liquid to seed the contents of the enclosure and thereby enhance the formation of a cloud therewithin;
   connecting a mouthpiece to the enclosure; and using the mouthpiece to translocate the formed cloud into the lungs; and further including the steps of: placing a one way check valve between a pump means and the enclosure to prevent subsequent loss of the medicated cloud.

15. The method of claim 14 wherein said enclosure is a transparent container which enables the patient to observe the formation of a cloud of medication therewithin.

16. The method of claim 14 and further including the steps of providing means by which the medicated powder is dispersed into the enclosure after the vapor pressure has been adjusted to thereby seed the vapor and enhance cloud formation.

17. The method of claim 14 wherein said mouthpiece is included for inhaling the contents of the enclosure; and further including means connected to the mouthpiece for forming an inlet from ambient into the enclosure;
   and wherein means are provided for dispersing medicated powder into the enclosure after the vapor pressure has been adjusted to thereby seed the vapor and enhance cloud formation.

18. A method of forming a cloud of vapor and medicine that can be inhaled to treat the lungs, comprising the steps of:
   isolating a liquid and evaporating a quantity of the liquid within an enclosure while adjusting the pressure within the enclosure to a value that enhances the subsequent formation of a cloud;
   selecting a quantity of treatment medicine that is in the form of a finely divided medicated powder; the quantity of powder selected provides a dose of medicine for ones lungs;
   dispersing the dose of medicated powder into the evaporated liquid to seed the contents of the enclosure and thereby enhance the formation of a cloud therewithin;
   connecting a mouthpiece to the enclosure; and using the mouthpiece to translocate the formed cloud into the lungs; and further including placing a one way check valve between a pump means and the enclosure to prevent subsequent loss of the medicated cloud;
   and further including the steps of providing means by which medicated powder is dispersed into the enclosure after the vapor pressure has been adjusted to thereby seed the vapor and enhance cloud formation.

19. The method of claim 18 wherein said mouthpiece is included for inhaling the contents of the enclosure; and further including means connected to the mouthpiece for forming an inlet from ambient into the enclosure;
   and wherein means are provided for dispersing medicated powder into the enclosure after the vapor pressure has been adjusted to thereby seed the vapor and enhance cloud formation.

* * * * *